(12) United States Patent
Palermo et al.

(10) Patent No.: US 12,123,843 B2
(45) Date of Patent: Oct. 22, 2024

(54) MICROFLUIDIC PATCH AND ELECTROCHEMICAL SENSING DEVICE

(71) Applicant: Consiglio Nazionale delle Ricerche, Rome (IT)

(72) Inventors: Vincenzo Palermo, Rome (IT); Vanesa Quintano, Rome (IT); Chiara Zanardi, Rome (IT)

(73) Assignee: Consiglio Nazionale delle Ricerche, Rome (IT)

( * ) Notice: Subject to any disclaimer, the term of this patent is extended or adjusted under 35 U.S.C. 154(b) by 151 days.

(21) Appl. No.: 18/011,032

(22) PCT Filed: Jun. 10, 2021

(86) PCT No.: PCT/EP2021/065667
§ 371 (c)(1),
(2) Date: Dec. 16, 2022

(87) PCT Pub. No.: WO2021/254881
PCT Pub. Date: Dec. 23, 2021

(65) Prior Publication Data
US 2023/0273138 A1 Aug. 31, 2023

(30) Foreign Application Priority Data
Jun. 16, 2020 (IT) .................. 102020000014398

(51) Int. Cl.
*G01N 27/12* (2006.01)
*A61B 5/00* (2006.01)
(Continued)

(52) U.S. Cl.
CPC ......... *G01N 27/12* (2013.01); *A61B 5/14517* (2013.01); *A61B 5/1477* (2013.01); *A61B 5/6804* (2013.01); *A61B 2562/043* (2013.01)

(58) Field of Classification Search
None
See application file for complete search history.

(56) References Cited

U.S. PATENT DOCUMENTS

2004/0053422 A1* 3/2004 Chan .................. B01D 71/02
436/178
2016/0339160 A1 11/2016 Bedworth et al.
(Continued)

OTHER PUBLICATIONS

Search Report, Written Opinion dated Aug. 11, 2021; Application No. PCT/EP2021/065667; 13 pages.

*Primary Examiner* — Eman A Alkafawi
*Assistant Examiner* — Suresh K Rajaputra
(74) *Attorney, Agent, or Firm* — Erik J. Overberger; RANKIN, HILL & CLARK LLP

(57) ABSTRACT

A microfluidic patch for separating specific species in biological fluids, comprising a flow layer comprising: a first porous portion to receive and carry a starting biological fluid containing related species; a multilayer membrane downstream the first porous portion and comprising a plurality of graphene-based sheets spaced among each other to define a plurality of parallel channels transversally interconnected and chemically functionalized to provide from the starting biological fluid an outgoing flow of specific species to be detected; and a second porous portion placed downstream the multilayer membrane to receive and carry the outgoing flow to be detected; the patch comprises a first upstream electrode and a first downstream electrode placed respectively upstream and downstream the multilayer membrane to foster the flow through the multilayer membrane from the first to the second porous portion.

14 Claims, 1 Drawing Sheet

Figure 1:
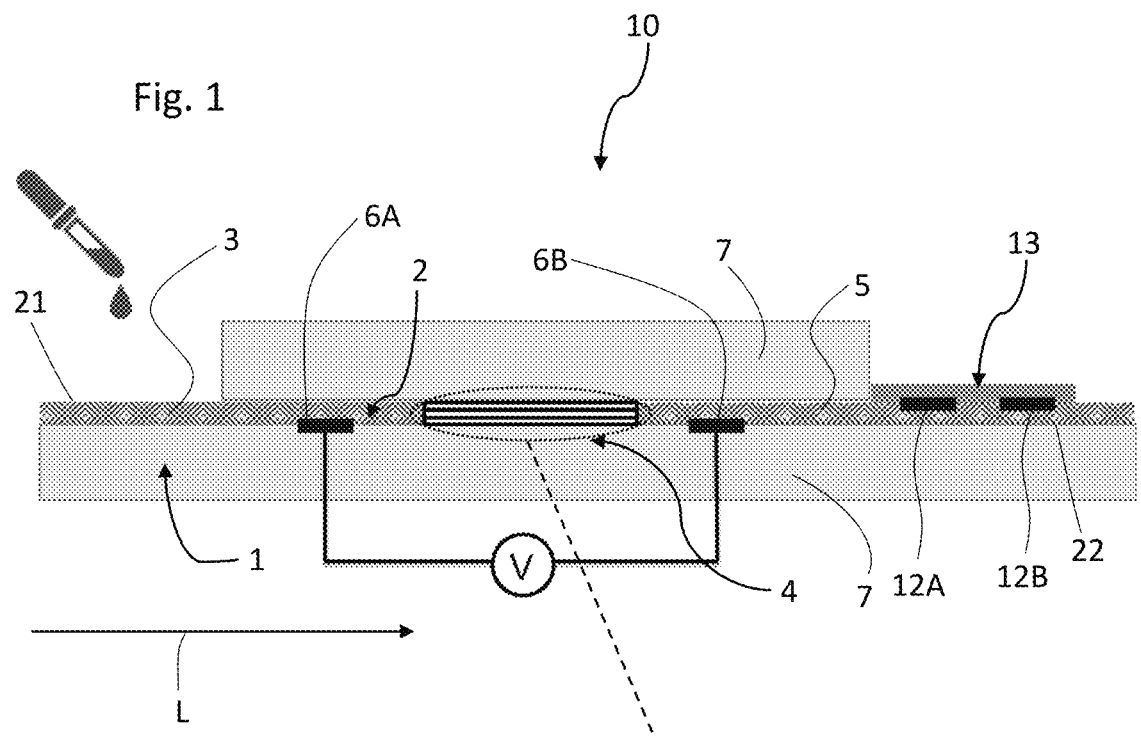

(51) Int. Cl.
*A61B 5/145* (2006.01)
*A61B 5/1477* (2006.01)

(56) References Cited

U.S. PATENT DOCUMENTS

2019/0069818 A1\* 3/2019 Prasad ............... A61B 5/14517
2020/0138347 A1\* 5/2020 Heikenfeld ........ A61B 5/14546

\* cited by examiner

MICROFLUIDIC PATCH AND ELECTROCHEMICAL SENSING DEVICE

TECHNICAL FIELD

The present invention relates to a wearable or non-wearable microfluidic patch and to an electrochemical sensing device that allow for the detection of specific species in biological fluids, e.g. sweat, blood or saliva, in order to monitor the health status of a human body.

DISCUSSION OF THE PRIOR ART

Wearable or non-wearable patches are used in the art to collect biological fluids from the human body for measuring physiological parameters.

It is also known to use an electrochemical sensing device that allows the detection of physiological parameters, for instance by detecting specific species in biological fluids, e.g. small ions are known in the state of the art.

Some commonly known electrochemical sensing devices comprise a patch onto which a biological fluid is deposited. The patch is configured to allow the flow of the biological fluid through it and to interact with the biological fluid therefore providing an outgoing flow of species. A measuring sensor connected to the patch is hence provided in order to carry out the analysis of the outgoing flow. In this way, specific species can be detected and analyzed.

Prior art document US 2020138347 A1 discloses a fluid sensing device capable of collecting a biological fluid sample, concentrating such collected sample with respect to a target analyte and finally measuring the analyte in the concentrated sample.

PRIOR ART PROBLEM

The outgoing flow obtained in the commonly known systems comprises many different species which are normally present in the biological fluid to be analyzed. However, these species may interfere with the detection of one or more species of interest.

As a consequence, the analyses of the specific species to be detected are not always precise and fully reliable.

SUMMARY OF THE INVENTION

The object of the present invention is to provide a microfluidic patch that allows for a more reliable and effective detection of one or more specific species of a biological fluid. Specifically, the object of the invention is to provide a device able to separate accurately the species of interest in order to obtain an outgoing flow that contains selectively the species to be detected. In this way, a higher sensitivity of the analysis is provided.

These and other objects are fulfilled by a microfluidic patch and by an electrochemical sensing device as defined in any of the accompanying claims. In the patch of the invention, an effective and selective filtering of the undesired species is provided, allowing the detection to be performed only on the species of interest.

BRIEF DETAILS OF THE DRAWINGS

Figure 2:
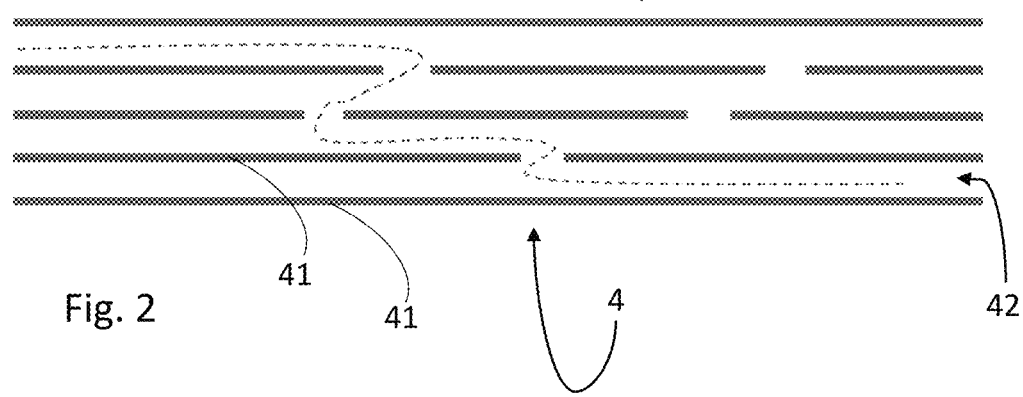

The characteristics and advantages of the present invention will result from the following detailed description of a possible practical embodiment, illustrated as a non-limiting example in the set of drawings, in which:

FIG. 1 shows a lateral view of an electrochemical sensing device comprising a microfluidic patch according to the present invention, FIG. 2 shows an enlarged sectional view of a detail of the electrochemical sensing device of FIG. 1.

The microfluidic patch and the electrochemical sensing device as shown in the accompanying figures shall be deemed to be schematically illustrated, not necessarily drawn to scale, and not necessarily representing the actual proportions of its parts.

DETAILED DESCRIPTION

FIG. 1 shows a microfluidic patch and an electrochemical sensing device according to the present invention. The patch is indicated with reference number 1 while the electrochemical sensing device is indicated with the reference number 10.

The microfluidic patch 1 according to the invention is for separating specific species in biological fluids in order to monitor health care and/or sport performance when training. Preferably, the microfluidic patch 1 can be of a wearable type, attachable to the skin or other human body surfaces to absorb the biological fluid of interest.

For instance, the wearable microfluidic patch 1 may be placed in contact with the skin of a human body to absorb sweat, for ions detection in sweat.

The microfluidic patch 1 may for example be integrated in sport clothes for sweat monitoring.

Alternatively, the microfluidic patch 1 can be of a non-wearable type, for instance configured to absorb a preciously collected biological fluid that is dripped onto it.

Particularly, the microfluidic patch 1 comprises a flow layer 2 that extends along a longitudinal direction L in a planar fashion.

Preferably, the flow layer 2 has a thickness of 100-300 microns. More preferably, the flow layer 2 has a thickness of 150 micron.

The flow layer 2 has a first surface 21 and an opposite second surface 22 parallel to said first surface 21.

The flow layer 2 is configured to allow a biological fluid deposited onto it to flow through it. Preferably, the flow layer 2 allows the biological fluid to flow through along the longitudinal direction L. The flow layer 2 is also configured to provide from a starting biological fluid an outgoing flow to be detected. The flow layer 2 is configured to interact with the starting biological fluid containing different species. Accordingly, the outgoing flow results from the interaction of the starting biological fluid with the flow layer 2, as it will be described more in detail in the following.

The flow layer 2 comprises a first porous portion 3. The first porous portion 3 has at least one part configured to receive the starting biological fluid. In other words, the first porous portion 3 has a part onto which the starting biological fluid can be deposited and absorbed. In fact, the first portion absorbs the biological fluid that is dripped onto it or by direct contact with a body surface, such as skin.

The first porous portion 3 is configured to carry along the longitudinal direction L the starting biological fluid containing related species. When the biological fluid is absorbed by the first porous portion 3, it travels through the first porous portion 3 by capillarity.

Preferably, the first porous portion 3 extends in a planar fashion along the longitudinal direction L.

Preferably, the first porous portion 3 is made at least partially of a paper-based material. According to an alternative embodiment, the first porous portion 3 is made of a plastic-based material. Advantageously, the lifetime of the first porous portion 3, and thus of the microfluidic patch 1, is longer than by employing a paper-based material.

The flow layer 2 also comprises a multilayer membrane 4 in fluid communication with the first porous portion 3. The multilayer membrane 4 is placed downstream the first porous portion 3 along the longitudinal direction L.

Preferably, the multilayer membrane 4 extends in a planar fashion along the longitudinal direction L.

The multilayer membrane 4 allows a flow of the biological fluid through it and interacts with the biological fluid thereby providing an outgoing flow of species.

Specifically, with reference to FIG. 2, the multilayer membrane 4 comprises a plurality of graphene-based sheets 41 parallel to each other. The graphene-based sheets 41 are spaced among each other so as to define a plurality of parallel channels 42 wherein species flow through. Preferably, the channels 42 extend along the longitudinal direction L. The channels 42 are also transversally interconnected among each other thus forming an interconnected network of channels 42.

More in detail, the graphene-based sheets 41 are chemically functionalized so as to act as sieve to provide from the starting biological fluid an outgoing flow of specific species to be detected. In other words, the multilayer membrane 4 filters the starting biological fluid by trapping undesired species. This is accomplished with the functionalization of the graphene-based sheets 41. In this way, only the species of interest to be detected can pass through the multilayer membrane 4.

Preferably, the functionalization is accomplished by covalent bonding of a specific moiety.

More preferably, according to the microfluidic patch 1 of the present invention, the graphene-based sheets 41 are functionalized with hydrophilic moieties. For instance, the graphene-based sheets 41 are functionalized with carboxylic groups.

According to an embodiment of the invention, the functionalized graphene-based sheets 41 comprise oxidized graphene, which is hydrophilic. Advantageously, oxidized graphene promotes a continuous flow of the biological fluid in a more efficient way if compared to bare graphene, which is hydrophobic.

Undesired species can be entrapped as a result of the functionalization. Therefore, the channels 42 feature dimensions allowing species in the biological fluid to collide with the walls of the channels 42 while flowing through them, i.e. with the graphene-based sheets 41.

Therefore, the selectivity of the multilayer membrane 4 is affected by the interspace and by the surface chemical functionalization of the graphene-based sheets 41.

Specifically, the graphene-based sheets 41 are spaced of a distance that allows species to easily flow through but also to allow a species flowing through to encounter at least one time the functionalized graphene-based sheets 41. Preferably, the graphene-based sheets 41 are spaced of a distance of 5-30 Angstrom, more preferably 6-10 Angstrom. Accordingly, channels 42 have dimensions ranging preferably from 5 to 30 Angstrom, more preferably from 6 to 10 Angstrom. Advantageously, species passing through are forced to interact with the chemical moieties on the surface of the graphene-based sheets 41.

On the other hand, the rate transport of species can be increased by increasing the graphene-based sheets 41 interspace. According to one embodiment, to increase the flow, the graphene-based sheets 41 are functionalized with chemical moieties acting as spacers. For example, the graphene-based sheets 41 are functionalized with organic molecules such as azobenzenes.

Accordingly, the graphene-based sheets interspace 41 can be specifically chosen for balancing a desired flow rate with appropriate selectivity.

The selectivity of the multilayer membrane 4 can be tuned also by tuning the length of the multilayer membrane 4. Specifically, the filtering efficiency increases by increasing the length of the multilayer membrane 4 and vice versa. The length of the multilayer membrane 4 is chosen so as the walls of the channels 42 entrap the highest possible number of undesired molecules. Therefore, the effectiveness of the sieving action can be tuned also by choosing appropriately the length for the multilayer membrane 4. Preferably, the multilayer membrane 4 features a longitudinal dimension of 0.5-3 centimeters, more preferably of 1-1.5 centimeters.

The total flow in the multilayer membrane 4 can be tuned also by tuning the number of graphene-based sheets 41, i.e. the thickness of the multilayer membrane 4.

According to one embodiment, the number of graphene-based sheets 41 stacked to form the membrane is 500-3000. Preferably the multilayer membrane 4 features a thickness of 1-5 microns, more preferably of 1.5 microns.

The structure of the multilayer membrane 4 given by the graphene-based sheets 41 allows for a better channels interconnectivity compared to other structures for example based on nanotubes or zeolites. The multilayer membrane 4 therefore also allows for higher flows while providing a good selectivity.

It is worth noting that the interconnected network of channels 42 can also be assembled in an easier fashion as compared to known zeolites or nanotubes-based structures.

The multilayer membrane 4 can be assembled for instance by filtration of graphene oxide water suspensions at room temperature. When filtering water, the packing of graphene-based sheets 41 occurs and provides the multilayer structure 4. The so-obtained multilayer membrane 4 is then functionalized depending on the specific species that are to be analyzed.

According to one embodiment, the microfluidic patch 1 is disposable as the multilayer membrane 4 saturates of the retained species, e.g. the undesired ions.

The flow layer 2 comprises also a second porous portion 5 in fluid communication with the multilayer membrane 4.

The second porous portion 5 is placed downstream the multilayer membrane 4 along the longitudinal direction L.

The second porous portion 5 is also in fluid communication with the first porous portion 3 through the multilayer membrane 4, which is interposed between the first porous portion 3 and the second porous portion 5.

Preferably, the second porous portion 5 extends in a planar fashion along the longitudinal direction L.

The second porous portion 5 is configured to receive and carry along the longitudinal direction L the outgoing flow to be detected.

Preferably, similarly to the first porous portion 3, the second porous portion 5 is made at least partially of paper-based material. Alternatively, the second porous portion 5 is made of a plastic-based material. Preferably, the first porous portion 3 and the second porous portion 5 are made of the same materials.

Preferably, the flow layer 2 is constituted by the sequence of the first porous portion, the multilayer membrane and the second porous portion placed contiguously and arranged in this order.

The microfluidic patch 1 further comprises two first electrodes 6A, 6B. In detail, the microfluidic patch 1 comprises means to connect the first electrodes 6 to an external device providing a bias.

The first electrodes 6A, 6B comprise a first upstream electrode 6A and a first downstream electrode 6B. The first upstream electrode 6A is placed upstream the multilayer membrane 4. The first downstream electrode 6B is placed respectively downstream the multilayer membrane 4. Specifically, the first electrodes 6A, 6B are configured to apply an electric bias to foster the flow through said multilayer membrane 4. Specifically, the electric bias is applied from the first downstream electrode 6B to the first upstream electrode 6A. The electric bias applied is ±0.1-1 V. Preferably, the electric bias applied is ±0.5 V. The applied electric bias is positive when an anionic filtration is desired. On the other hand, the applied electric bias is negative when a cationic filtration is desired. The flow through the multilayer membrane 4 occurs as it is mainly induced by the first electrodes 6A, 6B. In fact, a small part of the flow through the multilayer membrane 4 may also occur spontaneously by capillarity.

Preferably, the first electrodes 6A, 6B are placed in the first porous portion 3 and in the second porous portion respectively 5. More preferably, the first electrodes 6A, 6B contact the second surface 22. Even more preferably, the first electrodes 6A, 6B cross partially the first porous portion 3 and the second porous portion 5 in order to allow a flow through the first and the second porous portion 3, 5.

According to one embodiment, the first electrodes 6A, 6B are realized with conductive ink.

The first electrodes 6A, 6B specifically direct the flow through the multilayer membrane 4 along the longitudinal direction L, from the first porous portion 3 to the second porous portion 5.

The microfluidic patch 1 comprises also two hydrophobic layers 7. The two hydrophobic layers 7 sandwich the flow layer 2 and extend along the longitudinal direction L in a planar fashion. Specifically, the two hydrophobic layers 7 fully enclose the multilayer membrane 4 and enclose at least partially the first and the second porous portions 3, 5. This advantageously prevents leakage of flow of biological fluid especially from the multilayer membrane 4. Preferably, the hydrophobic layers 7 is also electrically insulating, to prevent current leakages.

The two hydrophobic layers 7 are arranged so as one of the two hydrophobic layers 7 is arranged along the first surface 21 so as to fully cover the multilayer assembly 4 and to partially cover the first and the second porous portions 3, 5. Preferably, the other of the two hydrophobic layers 7 is arranged to cover the whole second surface 22. Therefore, the uncovered area of the first porous portion 3 allows the inlet of the biological fluid in the flow layer 2. The uncovered area of the second porous 5 portion provides instead the outgoing flow to be detected.

According to the microfluidic patch 1 of the present invention, the hydrophobic layers 7 are polymer based. For example, the hydrophobic layers are realized in polydimethylsiloxane.

Advantageously, the microfluidic patch 1 is non-invasive and simple to use. Moreover, it allows real time detection of ions or other species of interest contained in biological fluids, with high sensitivity.

Advantageously, the dimension of the components of the microfluidic patch 1 can be selected to tune the efficiency of filtering for isolating the species of interest from biological fluids.

The present invention is also related to an electrochemical sensing device 10 for detecting specific species in biological fluids. The electrochemical sensing device 10 comprises the microfluidic patch 1 above described and a measuring sensor 13.

The measuring sensor 13 is connected to the microfluidic patch 1 and is configured to receive and analyze the outgoing flow flowing through the second porous portion 5.

Preferably, the measuring sensor 13 is connected to the microfluidic patch 1 at the second porous portion 5. More preferably, the measuring sensor 13 contacts the first surface 21. Accordingly, the hydrophobic layer 7 contacting the first surface is arranged to cover the second porous portion 5 up to the measuring sensor 13.

Preferably, the measuring sensor 13 can be attached in a removable fashion to the microfluidic patch 1, especially if the microfluidic patch 1 is disposable after a single use while the measuring sensor 13 is adapted to be reused. Alternatively, the measuring sensor 13 can be integrated in one piece with the microfluidic patch 1 so that the whole electrochemical sensing device 10 is disposable.

The measuring sensor 13 comprises at least one second electrode 12A placed downstream the first electrodes 6A, 6B at the second porous portion 5.

In a first embodiment not shown in the figures, the measuring sensor 13 comprises one second electrode 12A that is placed downstream the first downstream electrode 6B at the second porous portion 5. The second electrode 12A is configured to detect the conductivity of the species in the outgoing flow selected by the multilayer membrane 4 together with the first downstream electrode 6B.

In a second alternative embodiment shown in FIG. 1, the measuring sensor 13 comprises two second electrodes 12A, 12B, both the second electrodes 12A, 12B are placed downstream the first downstream electrode 6B at the second porous portion 5. Second electrodes 12A, 12B are configured to detect the conductivity of the species in the outgoing flow selected by the multilayer membrane 4. Preferably, the second electrodes 12A, 12B are interdigitated.

Preferably, each second electrode 12A, 12B contacts the first surface 21. More preferably, each second electrode 12A, 12B crosses partially the second porous portion 5. The electrochemical sensing device 10 according to the present invention is preferably aimed at detecting a biological fluid that is sweat. The specific species to be detected are specifically ions, e.g. potassium, sodium or chlorine ions.

Advantageously, the electrochemical sensing device 10 is non-invasive, simple to use and allows the real time detection of ions or other species of interest contained in biological fluids, with high sensitivity.

The invention claimed is:

1. Microfluidic patch for separating specific species in biological fluids, said patch comprising:
   a flow layer extending along a longitudinal direction in a planar fashion, said flow layer being configured to allow a biological fluid to flow through along said longitudinal direction, said flow layer being also configured to provide from a starting biological fluid an outgoing flow to be detected; said flow layer comprising:
      a first porous portion having at least one part configured to receive and carry along the longitudinal direction the starting biological fluid containing related species;
      a multilayer membrane in fluid communication with the first porous portion and placed downstream the first porous portion along the longitudinal direction, the multilayer membrane comprising a plurality of graphene-based sheets parallel to each other, the graphene-based sheets being spaced among each other so as to define a plurality of parallel channels extending along the longitudinal direction and transversally interconnected among each other, the graphene-based sheets being chemically functionalized so as to act as sieve to provide from the starting biological fluid an outgoing flow of specific species to be detected;

a second porous portion in fluid communication with the multilayer membrane, said second porous portion being placed downstream the multilayer membrane along the longitudinal direction, the second porous portion being configured to receive and carry along the longitudinal direction the outgoing flow to be detected;

two first electrodes comprising a first upstream electrode and a first downstream electrode placed respectively upstream and downstream the multilayer membrane, said first electrodes being configured to apply an electric bias to foster the flow through said multilayer membrane from the first porous portion to the second porous portion;

two hydrophobic layers sandwiching the flow layer and extending along the longitudinal direction in a planar fashion, said two hydrophobic layers fully enclosing the multilayer membrane and enclosing at least partially the first and the second porous portions.

2. Microfluidic patch according to claim 1, wherein the graphene-based sheets are functionalized with hydrophilic moieties.

3. Microfluidic patch according to claim 1, wherein said graphene-based sheets comprise oxidized graphene.

4. Microfluidic patch according to claim 1, wherein the flow layer has a first surface and an opposite second surface parallel to said first surface, one of the two hydrophobic layers being arranged along the first surface so as to fully cover the multilayer membrane and to partially cover the first and the second porous portions, the other one of the two hydrophobic layers being arranged to cover the whole second surface.

5. Microfluidic patch according to claim 1, wherein the hydrophobic layers are electrically insulating.

6. Microfluidic patch according to claim 1, wherein the hydrophobic layers are polymer based.

7. Microfluidic patch according to claim 1, wherein said graphene-based sheets are spaced of a distance of 5-30 Angstrom, preferably 6-10 Angstrom, the multilayer membrane featuring a longitudinal dimension of 0.5-3 centimeters, preferably 1-1.5 centimeters.

8. Microfluidic patch according to claim 1, wherein the graphene-based sheets are functionalized with chemical moieties acting as spacers to increase the flow.

9. Microfluidic patch according to claim 1, wherein the multilayer membrane features a thickness of 1-5 microns, preferably 1.5 microns.

10. Microfluidic patch according to claim 1, wherein the electric bias is applied from the first downstream electrode to the first upstream electrode, said electric bias ranging ±0.1-1 V.

11. Electrochemical sensing device for detecting specific species in biological fluids comprising:
a microfluidic patch according to claim 1,
a measuring sensor, connected to the microfluidic patch at the second porous portion, and configured to receive and analyze the outgoing flow.

12. Electrochemical sensing device as claimed in claim 11, wherein the measuring sensor comprises:
at least one second electrode placed downstream the first electrodes at the second porous portion, said second electrode being configured to detect the conductivity of the species in the outgoing flow selected by the multilayer membrane.

13. Electrochemical sensing device as claimed in claim 12, wherein the measuring sensor comprises one second electrode configured to detect the conductivity of the species in the outgoing flow together with the first downstream electrode.

14. Electrochemical sensing device as claimed in claim 12, wherein the measuring sensor comprises two second electrodes placed downstream the first electrodes at the second porous portion, to detect the conductivity of the species in the outgoing flow selected by the multilayer membrane, said second electrodes being interdigitated.

* * * * *